US005656468A

United States Patent [19]

Dorian et al.

[11] Patent Number: 5,656,468

[45] Date of Patent: *Aug. 12, 1997

[54] CELLS OR TISSUE COATED WITH NON-FIBROGENIC ALGINATE LESS THAN 200 μM THICK

[75] Inventors: Randel E. Dorian, Orinda; Kent C. Cochrum, Davis, both of Calif.

[73] Assignee: The Regents of the University of California, Oakland, Calif.

[ * ] Notice: The term of this patent shall not extend beyond the expiration date of Pat. No. 5,429,821.

[21] Appl. No.: 403,348

[22] Filed: Mar. 14, 1995

Related U.S. Application Data

[62] Division of Ser. No. 890,982, May 29, 1992, abandoned.

[51] Int. Cl.$^{6}$ .......................... C12N 11/10; C12N 11/00; C12N 11/04; C12N 13/00

[52] U.S. Cl. ...................... 435/178; 435/173.1; 435/174; 435/182

[58] Field of Search .................................... 435/175, 177, 435/180, 182, 173.1

[56] References Cited

U.S. PATENT DOCUMENTS

| | | | |
|---|---|---|---|
| 4,744,933 | 5/1988 | Rha et al. | 264/4.3 |
| 4,749,620 | 6/1988 | Rha et al. | 428/402.2 |
| 4,789,550 | 12/1988 | Hommel et al. | 424/493 |
| 5,429,821 | 7/1995 | Dorian et al. | 424/424 |

*Primary Examiner*—David M. Naff
*Attorney, Agent, or Firm*—Hana Verny

[57] ABSTRACT

An electrostatic process is used for coating a biological material with a uniform, continuous polymer layer by discharging a suspension of the biological material in a gelable coating polymer solution in a continuous stream through an orifice into an electrostatic field. The stream is attenuated to form droplets by maintaining an electrostatic voltage between the needle and the gelling solution which is sufficient to maintain an attraction of at least $1\times10^{-6}$ newtons on the stream of liquid leaving the needle, and the droplets are collected in a gelling solution. A preferred product is pancreatic islets having a continuous, smooth coating of high polymannuronate non-fibrogenic alginate having a thickness less than 200 μm such as about 20–200 μm. The alginate preferably contains less than 1 wt. % fucose, less than 0.5 wt. % sulfate and less than 0.01 wt. % phloroglucinol, is free of fibrinoogenic concentration of protein, and has a mannuronate to guluronate ratio of from 1.2 to 6. Preferably, the electrostatic field is formed by applying an electrostatic continuous DC voltage to each the needle and gelling solution so that the needle and solution have opposite charges.

18 Claims, 1 Drawing Sheet

10
6
4
2
14
(−)
12
8
16
18
(+)
20
22
24

8
(−)
26
16
18
20
(+)
24

CELLS OR TISSUE COATED WITH NON-FIBROGENIC ALGINATE LESS THAN 200 μM THICK

RELATIONSHIP TO APPLICATION

This is a divisional of application Ser. No. 07/890,982, filed on May 29, 1992, now abandoned.

FIELD OF THE INVENTION

This invention is directed to the field of medical transplants of cells and tissues, the manufacture of such transplants, and their use. In particular, this invention is directed to a process for forming thin, uniform, continuous coatings on tissue transplants such as pancreatic islet cells with a high degree of reproducibility.

BACKGROUND OF THE INVENTION AND PRIOR ART

Traditional medical treatments for functional deficiencies of secretory and other biological organs have focused on replacing identified normal products of the deficient organ with natural or synthetic pharmaceutical compositions. For example, for treating insulin-dependent diabetes mellitus, also known as type I or juvenile onset diabetes, the normal secretion of insulin by the islets of Langerhans in the pancreas must be replaced since functional islets are no longer present in the pancreas. This pancreatic function is emulated by administering insulin, titrating the injections in response to blood glucose level measurements. At best, the normal production of the islets are poorly approximated.

Organ replacement has also been applied. This has generally required continuous use of immunosuppressive agents to prevent immunological rejection of the organ, depriving the patient of the full protective function of the immune system against diseases. It has provided permanent relief only for a limited group of organs.

Attempts to transplant organ tissues into genetically dissimilar hosts without immunosuppression have been generally defeated by the immune system of the host. Prior to this invention, application of effective protective barrier coatings to isolate the transplant tissues from the host immune system has not proven to be medically practical for a number of reasons. The coating materials were incompatible with the host system or unsuitable for other reasons. Encapsulation or coating processes previously developed did not yield reproducible coatings having the desired permeability and thickness required for the transplant tissue to have a long and effective functioning life in the host.

To protect transplants from destruction by the immune response of the host animal, various attempts have been made to create a protective barrier between the transplant tissue or cells and the immunological components of the host's system. T. M. S. Chang, *Science* 146:524–525 (1964) described the microencapsulation of erythrocyte hemolysate and urease in semi-permeable polyamide membranes. These microcapsules did not survive for long when injected into the blood stream. K. Mosbach et al, *Acta Chem. Scand.* 20:2807–2812 (1966) and T. M. S. Chang et al, *Can. J. Psysiol.* and *Pharmacology* 44:115–128 (1966) described the preparation of semi-permeable microencapsulated microbial cells and viable red blood cells, the latter article mentioning the possibility of using injections of encapsulated cells for organ replacement therapy.

Encapsulation methods applied to make these materials have comprised a procedure for forming droplets of the encapsulating medium and the biological material and a procedure for solidifying the encapsulating medium. Agarose encapsulated materials have been formed by chilling an emulsion of agarose droplets containing biological materials as shown by Nilsson et al, *Nature* 302:629–630 (1983) and Nilsson et al, *Eur. J. Appl. Microbiol. Biotechnol.* 17:319–326 (1983). Injection of droplets of polymer containing biological materials into a body of coolant such as a concurrently liquid stream has been reported by Gin et al, *J. Microencapsulation* 4:329–242 (1987).

Alginates form a gel when reacted with calcium ions. Alginate droplets have been formed by emulsifying a solution of sodium alginate containing cellular material to form droplets of sodium alginate and cells, and gelling the droplets with calcium chloride in U.S. Pat. No. 4,352,883. Alginate droplets have also been formed with a syringe and pump to force droplets from a needle, using a laminar flow air knife to separate droplets from the tip, the droplets being gelled by collecting them in a calcium chloride solution in U.S. Pat. No. 4,407,957. Alginate droplets have also been formed by the simple procedure of expelling them from a hypodermic needle and allowing the droplets to fall in to a calcium chloride solution, as described by Nigam et al, *Biotechnology Techniques* 2:271–276 (1988). Droplets have also been injected into a concurrently flowing stream containing calcium chloride in U.S. Pat. No. 3,962,383. Spraying alginate solutions through a spray nozzle to form a mist of droplets which were collected in a calcium chloride solution was reported by Plunkett et al, *Laboratory Investigation* 62:510–517 (1990). These methods have not proven effective for mass production of coatings required for successful transplantation.

Hommel et al in U.S. Pat. No. 4,789,550 disclose the formation of alginate droplets using a combination of a needle and a square wave electrical electrostatic voltage to form uniform droplets. The alginate solution was forced from the tip of a needle to form a droplet, and the droplet was pulled from the needle by a changing electrostatic field between the needle tip and a calcium chloride solution placed below the needle tip. The droplet received a charge of one polarity from the needle, opposite to the charge in the calcium chloride solution. When the voltage difference between the droplet and the oppositely charged calcium chloride solution reached a value at which the attraction by the solution on the droplet exceeded the force of interfacial tension holding the droplet on the needle tip, the droplet was pulled free to fall into the calcium chloride solution. The electrostatic field was fluctuated using a square wave form to create a succession of voltages crossing the threshold voltage at which droplets were pulled free from the needle, thus producing a continuous series of droplets, one per square wave cycle. The process was not found to provide the small droplets and thin coatings required for effective transplantation.

OBJECTS AND SUMMARY OF THE INVENTION

It is one object of this invention to provide an apparatus and process which produces uniform, smooth, continuous coatings on transplantation tissues and cells, the coatings having a reproducible thickness of less than 200 μm.

It is another object of this invention to provide an apparatus and process which produces coatings of physiologically non-toxic, host-compatible materials on transplantation tissues and cells, the coatings having the permeability required for the diffusion of nutrients and biological materials required for the long life and effective function of the transplanted tissues and cells in the transplant host, while providing effective protection to the transplanted tissues from the host immune system.

In summary, the process of this invention is a procedure for coating a biological material with a uniformly sized coating of polymer comprising the steps of dispersing the biological material in an aqueous solution of the polymer. The suspension is released from an orifice in a continuous stream above an electroconductive liquid capable of gelling the polymer. At the same time a first voltage is applied to the orifice and a second voltage is applied to the electroconductive liquid. The electric voltage between the orifice and the electroconductive liquid and the electric charge of the released droplets attenuate the stream of aqueous solution to form a continuous stream of droplets having a reproducible size. The droplets are then gelled by collecting the droplets in the electroconductive liquid to form particles with a continuous, smooth polymer coating on the biological material. Preferably, the polymer solution has a viscosity of from about 50 to about 150 centipoises and the orifice has a diameter of from about 0.1 to 2 mm.

In a preferred embodiment, the polymer solution is a sodium alginate solution, and the electroconductive liquid is an aqueous electrolyte solution containing a concentration of calcium ions sufficient to gel the alginate. Optimally, the polymer solution contains an alginate having a mannuronate to guluronate moiety ratio of from 1.2 to 6, the alginate being free from impurities which would impair viability and long life of tissue transplants coated with the calcium reaction product thereof.

The voltage difference between the orifice and the electroconductive liquid is sufficient to provide a continuous attraction for the liquid leaving the needle of at least $1\times10^{-6}$ newtons.

The coated products of this process are a further aspect of this invention. These are preferably coated cores of viable, physiologically active, tissue cells such as pancreatic islet cells having a non-fibrogenic coating of alkline earth metal alginate coating thickness of from about 20 to about 200 μm.

DETAILED DESCRIPTION OF THE INVENTION

Figures 1, 2:
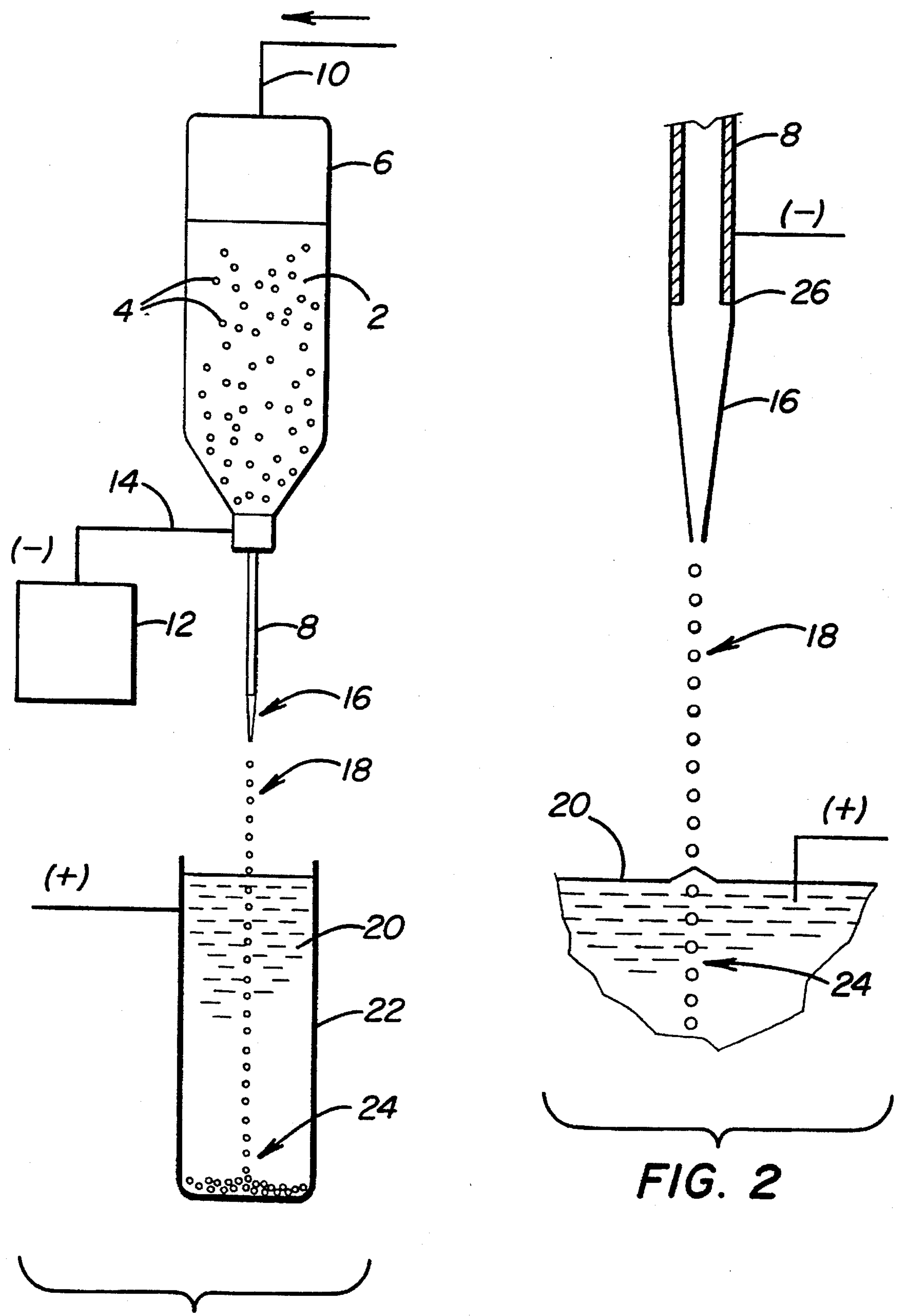
FIG. 1 is a schematic representation of the electrostatic apparatus of this invention.
FIG. 2 is an enlarged schematic representation of the liquid stream showing the stream attenuation and drop formation in the electrostatic apparatus of this invention.

The apparatus and process of this invention is highly effective for applying uniform, continuous, smooth coatings on transplantation tissue cells with a high degree of control and reproducibility and at coating rates which are medically practical. The coated products have the effective volumes and diameters required for transplantation by injection through standard needle gauges.

The term "transplant", as used herein, is defined to include all living tissues, cells, and biologically active substances or material intended to be implanted into the body of a host animal and the act of implanting these tissues and cells. These tissues and cells include, without limitation, tissue and cells removed from a donor animal, tissue and cells obtained by incubation or cultivation of donor tissues and cells, cells obtained from viable cell lines, biologically active products of cells and tissues, and the like.

Any type of tissue or cells for which transplantation is desired can be coated and transplanted according to this invention. The most important tissues for transplants are secretory organ tissues, where transplantation from a donor organ to a host animal is desired to at least partially replicate the donor organ's action in the host system. Preferred donor tissues are pancreatic islets, hepatic cells, neural cells, renal cortex cells, vascular endothelial cells, thyroid cells, adrenal cells, thymic cells and ovarian cells.

We have found that for secretory tissues such as pancreatic islets, the thickness of protective porous coatings should be in the range of from 20 to 200 μm. The coatings must also have the permeability required to permit effective diffusion of nutrients and other essential biological materials to the transplanted tissues and passage of transplant tissue products therefrom into the host or donor system. The coatings must simultaneously exclude immunologically effective concentrations of agents of the host immune system from the transplant tissue.

The apparatus of this invention will produce transplant tissue coatings having these essential characteristics with high efficiency and product volumes required to replace or supplement an organ's function in a human host.

Referring to the drawings, FIG. 1 is a schematic representation of the electrostatic apparatus of this invention, and FIG. 2 is an enlarged schematic representation of the liquid stream showing the stream attenuation and drop formation in the electrostatic field created by the apparatus. A coating solution 2 containing electrolytes and suspended transplant tissue fragments or cells 4 is provided in a reservoir 6. An orifice outlet for a thin stream of coating solution is provided by needle 8 communicating with the liquid in the reservoir. Pressure for expelling liquid from the reservoir 6 through the needle 8 can be provided by any conventional system, such a gas pressure supply line 10 or alternatively, a plunger, pump or other conventional system.

An electrostatic voltage is applied to the metal needle 8 or to the solution from a conventional high DC voltage source such as a van de Graaff generator or other conventional high voltage DC power supply 12 through electrical connection 14. The voltage must be constantly at a level sufficient to continuously form an attenuated stream of suspension 16 forming a continuous series of droplets 18 having a constant size. The droplets are collected in a solution 20 contained in droplet collector 22, the solution 20 having a charge opposite to the charge of the needle 8. Solution 20 provides the reagents or conditions required to solidify the droplets, forming the coated transplantation products 24.

In the embodiment shown in FIG. 1, the needle has a negative charge and the an electroconductive collection container 22 has a positive charge. It will be readily apparent to a person skilled in the art that alternative configurations can be provided to yield a high voltage electrostatic potential of opposite charges between the needle 8 and the solution 20. For example, the polarities can be reversed, and the needle 8 can have a positive charge relative to the solution 20.

Without the electrostatic attraction of the solution 20 for the liquid leaving the needle 8, large individual droplets would be formed, their size being determined only by gravitational force, the interfacial tension of the solution and the flow rate, yielding a coating with excessive thickness. We have found that coatings of the desired size can be obtained when the continuous attraction of the solution 20 for the liquid leaving the needle is at least about $1\times10^{-6}$ newtons for coating solutions having a viscosity of from about 50 to 150 centipoises. In prior art processes, needle size must be reduced to produce smaller droplets, requiring increased pressures and placing a practical lower limit on the sizes which can be obtained. Since the particle sizes produced by the process of this invention are independent of the needle size, the smallest particles can be produced, even with the largest needles. This permits small particles to be formed from viscous solutions with a minimum of pressure.

For needle orifices 8 having inner diameters of from 0.1 to 2 mm, electrostatic DC voltages of from 1 to 400 KV have been found to be satisfactory for operation in air under ambient conditions. Currents ranging from 0.2 μA to 3.5 μA are suitable.

The process of this invention for coating a biological material such as transplant tissues with a uniformly sized coating of polymer using the apparatus described above comprises dispersing the biological material in an aqueous solution of the polymer 2. Then the aqueous solution is discharged from an orifice 8 in a continuous stream 16 above an electroconductive liquid 20 capable of gelling the polymer while placing an electrical charge of one polarity on the stream while it is being discharged. An electric charge of opposite polarity is maintained on the electroconductive liquid 20, the electric charge being sufficient to continuously attenuate the stream of aqueous solution to form a continuous stream of droplets having a reproducible size. The polymer droplets are then gelled to form a continuous polymer coating on the biological material and smoothing the coating to form spherical coated particles by collecting the droplets in the electroconductive liquid 20. Preferably, the polymer solution has a viscosity of from about 50 to about 150 centipoises, and the orifice has a diameter of from about 0.2 to 0.8 mm.

This process can be used to coat any transplant of biologically active agents, tissues or cells. It is particularly advantageous for coating transplantation tissues such as pancreatic islets, hepatic cells, other endocrine tissues and cells, and neural cells.

Coating agents must be physiologically acceptable and non-toxic to the biologically active material being coated and to the host or recipient organism and its tissue. The coating must be non-fibrogenic to avoid encapsulation by the host immune system. Coatings having an outer negative charge such as polysaccharides (agarose, etc.) and alginates are most suitable. Particularly effective coating materials are the highly purified alginates such as described in copending application Ser. No. 07/891564 filed on May 29, 1992 now U.S. Pat. No. 5,429,821. These alginates are free from fibrogenic concentrations of fucose, sulfate, phloroglucinol and protein moieties, any amount in the coating of fucose moieties being less than 1 wt. %, of sulfate moieties being less then 0.5 wt. %, and of phloroglucinol moieties being less than 0.01 wt. %. The alginates should have an average chain length corresponding to a polymer molecular weight of from about 10 to 200 kilodaltons and preferably from 12 to 80 kilodaltons. Molecular weights and average chain lengths below these ranges yield a calcium alginate gel with a physical strength which is insufficient to provide the integrity required for implantation and long term exclusion of immune system agents.

The mannuronate to guluronate molar ratio of the coating polymer should be from 1.2 to 6 and is preferably from 1.5 to 2.5. A mannuronate to guluronate molar ratio above these ranges is undesirable because the coating obtained therewith tends to swell and weaken when placed in the host body, increasing the permeability and lengthening the nutrient diffusion path through the coating.

When the polymer solution is a sodium alginate solution, the solution 20 can be an aqueous, electroconductive alkaline earth metal salt solution such as an aqueous solution containing a level of calcium and/or magnesium ion sufficient to react with and gel the alginate coating. The calcium ion concentration, as calcium chloride, should be at least 0.5 weight percent of the solution.

When the polymer solution is an agarose solution, the droplets can be gelled by cooling with air and collected.

The products of this process are coated cores of viable transplant, i.e., physiologically active, tissue cells such as pancreatic islet cells having a coating thickness is from 20 to 200 μm.

This invention is further illustrated by the following specific but non-limiting examples. Percents are given in weight percents and temperature in degrees Centigrade unless otherwise specified.

EXAMPLE 1

Sodium Alginate Preparation

Low viscosity sodium alginate (LV Alginate, KELCO DIV. of Merck & Co.) isolated from *Macrocystis purifera* was dissolved in a neutral solution of HEPES buffered saline, clarified by centrifugation, and filtered to remove particulates. The solution was passed through perchlorate-bleached activated charcoal (Mallinckrodt activated charcoal powder) to remove organic contaminants such as polyphenols. The resulting clear solution was precipitated by adding sufficient 1N HCl to reduce the solution pH to 2. The precipitate was pelleted by centrifugation and redissolved in aqueous sodium chloride solution containing sufficient EDTA (about 2 ppm) to chelate any trace calcium and magnesium ions which were present in the sodium chloride reagent. The solution was reprecipitated by adding ethanol, and the precipitate was separated from the solution and redissolved in a 1M solution of potassium chloride to redissolve the guluronate-rich fraction. The insoluble material remaining was pelleted by centrifugation, redissolved in aqueous NaCl solution containing sufficient EDTA (about 2 ppm) to chelate any trace calcium and magnesium ions which were present in the sodium chloride reagent, and reprecipitated with ethanol. The precipitate was collected on a fine mesh sieve, and the remaining salt and trace organic impurities were washed from the precipitate with copious volumes of aqueous solutions of ethanol with NaCl (with EDTA) of sequentially increasing proportions of alcohol and decreasing salt concentration. The material was finally washed in absolute ethanol, the excess alcohol removed, and the material was fluffed and dried at 80° C. in a circulating oven.

The resulting dry material was dissolved in HEPES-buffered dilute sodium citrate, 0.01M, with NaCl added to isoosmolarity and filtered through a 0.1 micron membrane.

EXAMPLE 2

Pancreatic Suspension Islet Preparation

Pancreatic islets isolated from rat were washed with isotonic saline, were suspended in an alginate solution prepared by dissolving the alginate prepared by the procedure of Example 1 at a concentration of 10,000 islets per ml in 1.5 wt. % purified alginate in 10 mM HEPES, 0.01M sodium citrate, containing sufficient sodium chloride required for isoosmolarity (about 0.81 wt. %), the final solution having a viscosity of about 50 centipoises at 32° C. The islets had an approximate average diameter of 150 μm.

This procedure was repeated with dog islets.

EXAMPLE 3

Pancreatic Islet Coating

Using a DC electrostatic voltage of 8 KV provided by a van de Graaff generator between needle tip and grounded 0.117M aqueous calcium chloride solution at ambient temperature, a suspension of pancreatic islets (25 islets per μL) prepared by the procedure of Example 2 was passed through a 20 gauge needle at a flow rate of approximately 200 μl/min. The suspension emerged from the needle as a thin, attenuated stream which transformed into droplets, the droplets being collected in the calcium chloride solution. The droplets were gelled by reaction with the calcium ion in the solution. The calcium alginate coatings on the islets were smooth and uniform and had an approximate thickness of about 130 μm. The total coated particle had an average diameter of about 360 μm.

This process was repeated with dog islets prepared by the procedure of Example 2.

EXAMPLE 4

Pancreatic Islet Transplant into Diabetic Mice (IP)

Host Balb/C mice were rendered diabetic by IP injection of streptozocin (250 mg/kg) at 50 mg/mL in 0.1M citrate buffer, pH 4.5 several days prior to transplant.

Coated dog islets prepared by the procedure of Example 3 were injected IP, 2000–3000 islets per mouse, into one group of mice. The mice became and have remained euglycemic as of the filing date hereof.

Spheres formed from the same alginate (without cells) were injected IP into a control group of Balb/C mice. The mice were sacrificed weekly for up to 16 weeks. The alginate spheres were examined histologically and found to be free from fibrosis and macrophages.

EXAMPLE 5

Pancreatic Islet Transplant into Diabetic Dog

A dog's spleen was injected via the splenic vein using a 16 gauge needle with coated dog islets prepared by the procedure of Example 3. The coated islets were suspended in saline, 10 mM HEPES, containing 10 mM $Ca^{++}$ ions at a density of 1300 coated islets per mL of injection volume.

Three weeks after transplantation, the dog was anesthetized, and the splenic artery and vein were cannulated to determine if the coated islets in the spleen were producing insulin. The dog received a dextrose bolus (5 mg/Kg) via a tributary of the splenic artery to stimulate insulin release from the coated islets in the spleen. Blood samples were taken from the splenic artery and vein 10 min prior to the bolus injection and at 2 min intervals following the dextrose injection.

Insulin was detected in the splenic vein following the dextrose challenge (14–40 uIU/mL). Before the dextrose challenge, the splenic vein insulin levels were baseline (2–2.5 uIU/mL).

Histology of the coated islets in the spleen demonstrated viable islets with no associated fibrosis or macrophages. These results indicate that the coating protected the transplanted islets and that the islets had an insulin response following a dextrose challenge.

The invention claimed is:

1. Coated cells for transplanting wherein the cells have a smooth, uniform and continuous coating less than 200 μm thick, consisting essentially of a non-fibrogenic alginate, said coated cells produced by a process comprising the steps:

(a) dispersing the cells in an aqueous solution of the non-fibrogenic alginate containing less than 1 wt. % fucose, less than 0.5 wt. % sulfate, less than 0.01 wt. % phloroglucinol and being free from fibrinogenic concentration of protein, and having a mannuronate to guluronate ratio of from 1.2 to 6, to form a suspension;

(b) discharging the suspension of step (a) from a reservoir and through an orifice of an electrostatic apparatus in a continuous attenuated stream forming droplets in an electrostatic field created by said electrostatic apparatus, said droplets expelled from the orifice placed above an electroconductive liquid capable of gelling the polymer;

(c) applying a first electrostatic continuous DC voltage on the orifice and a second electrostatic continuous DC voltage on the electroconductive liquid of step (b) generating a continuous constant electrical potential while the suspension is being discharged from the orifice in the continuous stream, the electrical potential being sufficient to continuously attenuate the stream of suspension to form a continuous stream of droplets having the same size; and (d) collecting the formed droplets in the electroconductive liquid capable of gelling the alginate to form a continuous, smooth and uniform coating on the cells less than 200 μm thick resulting in formation of said coated cells;

wherein the alginate solution of step (a) has a viscosity of from about 30 to about 250 centipoises;

wherein the orifice of step (b) has a diameter of from about 0.1 to 2 mm; and wherein the electroconductive liquid of step (b) comprises an aqueous electrolyte solution containing a concentration of alkaline earth metal ions sufficient to gel the alginate.

2. The coated cells of claim 1 wherein the voltage potential between said first and second voltages is sufficient to provide a continuous attraction of at least $1\times10^{-6}$ newtons for the liquid leaving the orifice.

3. The coated cells of claim 2 wherein the coated cells are pancreatic islet cells.

4. The coated cells of claim 3 wherein the coating has a thickness of from about 20 to about 200 μm and wherein the electrolyte solution is calcium chloride.

5. The coated cells of claim 4 wherein the mannuronate to guluronate molar ratio of the alginate coating is from 1.5 to 2.5.

6. The coated cells of claim 5 wherein the electrostatic continuous DC voltage of step (c) is from 1 to 400 KV.

7. The coated cells of claim 6 wherein the alginate has a molecular weight from about 10 to about 200 kilodaltons.

8. The coated cells of claim 7 wherein a calcium ion concentration is at least 0.5 wt. % of the aqueous solution.

9. A coated pancreatic islet tissue for transplanting coated with a smooth, uniform and continuous coating less than 200 μm thick, consisting essentially of a non-fibrogenic alginate, said coating produced by a process comprising the steps:

(a) dispersing the pancreatic islet tissue in an aqueous solution of the non-fibrogenic alginate containing less than 1 wt. % fucose, less than 0.5 wt. % sulfate, less than 0.01 wt. % phloroglucinol and being free from fibrinogenic concentration of protein, and having a mannuronate to guluronate moiety ratio of from 1.2 to 6, to form a suspension;

(b) discharging the suspension of step (b) from a reservoir and through an orifice of an electrostatic apparatus in a continuously attenuated stream forming droplets in an electrostatic field created by the apparatus, said droplets expelled from the orifice placed above an electroconductive liquid capable of gelling the polymer;

(c) applying a first electrostatic continuous DC voltage on the orifice and a second electrostatic continuous DC voltage on the electroconductive liquid of step (b) generating a continuous constant electrical potential while the suspension is being discharged from the orifice in the continuous stream, the electrical potential being sufficient to continuously attenuate the stream of suspension to form a continuous stream of droplets having the same size; and (d) collecting the droplets in the electroconductive liquid capable of gelling the alginate and forming a continuous, smooth and uniform coating on the pancreatic islet tissue less than 200 μm thick resulting in formation of said coated pancreatic islet tissue;

wherein the solution of step (a) has a viscosity of from about 50 to about 150 centipoises;

wherein the orifice of step (b) has a diameter of from about 0.1 to 2 mm; and wherein the electroconductive liquid of step (b) comprises an aqueous electrolyte solution containing a concentration of alkaline earth metal ions sufficient to gel the alginate.

10. The coated pancreatic islet tissue of claim 9 wherein the electrolyte solution is calcium chloride.

11. The coated pancreatic islet tissue of claim 10 wherein the coating has a thickness of from about 20 to about 200 μm.

12. The coated pancreatic islet tissue of claim 11 wherein the coating has a thickness of about 130 μm and the electrolyte is calcium chloride.

13. The coated pancreatic islet tissue of claim 12 wherein the voltage potential between said first and second voltages is sufficient to provide a continuous attraction of at least $1\times10^{-6}$ newtons for the liquid leaving the orifice.

14. The coated pancreatic islet tissue of claim 13 wherein the mannuronate to guluronate molar ratio of the alginate coating is from 1.5 to 2.5.

15. The coated pancreatic islet tissue of claim 14 wherein the alginate has a molecular weight from about 10 to about 200 kilodaltons.

16. The coated pancreatic islet tissue is wherein the electrostatic continuous DC voltage of step (c) is from 1 to 400 KV.

17. The coated pancreatic islet tissue of claim 16 wherein a ratio of a current necessary to generate the electrostatic continuous DC voltage of step (c) is from 0.2 to 3.5 μA.

18. The coated pancreatic islet tissue of claim 17 wherein a calcium ion concentration is at least 0.5 wt. % of the aqueous solution.

* * * * *